(12) United States Patent
Dubois et al.

(10) Patent No.: US 8,295,581 B2
(45) Date of Patent: Oct. 23, 2012

(54) METHOD AND APPARATUS FOR DETECTING DEFECTS IN OPTICAL COMPONENTS

(75) Inventors: Frédéric Dubois, Charenton le Pont (FR); Fabrice Gibrat, Charenton le Pont (FR); Guy Schott, Charenton le Pont (FR); Philippe Raulot, Charenton le Pont (FR)

(73) Assignee: Essilor International (Compagnie Generale d'optique), Charenton le Pont (FR)

( * ) Notice: Subject to any disclaimer, the term of this patent is extended or adjusted under 35 U.S.C. 154(b) by 396 days.

(21) Appl. No.: 12/595,787

(22) PCT Filed: Apr. 14, 2008

(86) PCT No.: PCT/EP2008/054502
§ 371 (c)(1),
(2), (4) Date: Apr. 1, 2010

(87) PCT Pub. No.: WO2008/125660
PCT Pub. Date: Oct. 23, 2008

(65) Prior Publication Data
US 2010/0290694 A1  Nov. 18, 2010

(30) Foreign Application Priority Data
Apr. 13, 2007 (EP) .................................. 07290457

(51) Int. Cl.
*G06K 9/00* (2006.01)
(52) U.S. Cl. .................. 382/141; 356/237.1; 356/237.6; 356/604; 382/145
(58) Field of Classification Search .................. 382/141, 382/145; 356/237.1–237.6, 604
See application file for complete search history.

(56) References Cited

U.S. PATENT DOCUMENTS

| 4,641,972 A | 2/1987 | Halioua et al. |
| 4,776,698 A * | 10/1988 | Crosdale ........................ 356/493 |
| 6,208,412 B1 * | 3/2001 | Ladewski .................... 356/239.1 |
| 7,382,471 B2 * | 6/2008 | Franke et al. ................. 356/604 |
| 7,990,531 B2 * | 8/2011 | Clements et al. .......... 356/239.2 |

FOREIGN PATENT DOCUMENTS

| EP | 0 685 733 | 12/1995 |
| EP | 1 065 498 | 1/2001 |
| WO | WO 02/42715 | 5/2002 |

OTHER PUBLICATIONS

M-L Zani, "Une autre manière de "voir" les défauts de surface", Mesures, vol. 733, pp. 73-77, Mar. 2001, XP002452891.

* cited by examiner

*Primary Examiner* — Tarifur Chowdhury
*Assistant Examiner* — Isiaka Akanbi
(74) *Attorney, Agent, or Firm* — Cozen O'Connor (57) ABSTRACT

A method is disclosed for detecting defects in an optical component to be tested, such as a lens comprising the steps of: providing a structured pattern, recording the reflected or transmitted image of the pattern on the optical component to be tested, phase shifting the pattern and recording again similarly the reflected or transmitted image, calculating the local phase and amplitude images of the optical component to be tested, calculating a model image of a defect free optical component and determining corresponding phase and amplitude images of the defect free model optical component, comparing phase and amplitude images of both optical component to be tested and defect free model optical component, determining suspect zones in the optical component to be tested, and applying a metrics to separate dust and noise from other defects.

20 Claims, 9 Drawing Sheets

METHOD AND APPARATUS FOR DETECTING DEFECTS IN OPTICAL COMPONENTS

RELATED APPLICATIONS

This is a U.S. national stage of application No. PCT/EP2008/054502, filed on Apr. 14, 2008.

This application claims the priority of European application no. 07290457.6 filed Apr. 13, 2007, the entire content of which is hereby incorporated by reference.

The present invention relates to a method and apparatus for detecting defects in optical components such as lenses, particularly cosmetic defects consisting of surface flaws and occlusions.

Optical components of transparent material, for example, optical ophthalmic lenses, must be tested for defects prior to their utilization, particularly for surfaces flaws such as scratches, smears, cracks, chips, stains, and for occlusions such as bubbles or streaks. Limit values of tolerable flaws are established in internationally recognized standards for precision optics, specifically DIN 3140 or MIL-0-13830 or less stringent standards used by the ophthalmic industry, such as DIN 58203.

Conventionally, the testing is carried out by visual inspection by trained personnel, mostly in a darkened room. Such a procedure is expensive, not sufficiently objective and not sufficiently reliable. Therefore, efforts are being made to develop methods and devices for the automatic and objective testing of optical components.

Numerous testing methods have been studied and used to try to determine the quality of optical components, but difficulties remain to obtain reliable results. Among the difficulties which are encountered the following can be cited:

- measurement time is long to obtain a reliable result and dramatically slows the control process;
- type of defects cannot be classified properly and good samples may be rejected;
- expensive devices are required for carrying out the test method;
- the test method needs complex standardization or calibration procedures.

Thus, the object of the present invention is to provide improved, reliable and reasonably simple and inexpensive method and apparatus for testing optical components for defects.

This object is solved in accordance with the invention by a method for detecting defects in an optical component to be tested, such as a lens, comprising following steps:

- providing a structured pattern,
- recording the reflected or transmitted image of the pattern on the optical component to be tested,
- phase shifting the pattern and recording again similarly the reflected or transmitted image,
- calculating the local phase and amplitude images of the optical component to be tested,
- calculating a model image of a defect free optical component and determining corresponding phase and amplitude images of the defect free model optical component,
- comparing phase and amplitude images of both optical component to be tested and defect free model optical component,
- determining suspect zones in the optical component to be tested,
- applying a metrics to separate dust and noise from other defects.

Both reflected or transmitted image capture and treatment are possible. Using the wording "similarly" for the second image recording step means that if the first image recording step is directed to reflected, respectively to transmitted image, the second image recording step will be directed to a reflected, respectively to a transmitted image.

Thus, method, in accordance with the present invention, provides an effective inspection of optical components such as finished or semi finished lenses, where the range of inspection includes both optical surfaces and said bulk of the component.

The present invention provides for a method enabling to check all kinds of lenses and substrates, particularly ophthalmic lenses, e.g. single vision (spherical, torical), bi-focal, progressive, aspherical, etc. and semi-finished lenses, and differentiating between cosmetic defects of an optical component, such as flaws and occlusions, on the one hand, and dust on its surfaces, on the other hand, Independence of inspection from said dust, thereby allows inspection of optical components without requiring their prior cleaning.

According to embodiments of the present invention:

- the calculated phase and amplitude images of the optical component to be tested are obtained by image merging of vertical curvature $I_v$ and horizontal curvature data.
- the optical component is a progressive addition lens comprising standard engravings and where the engravings are used to determine the attitude of the lens to be tested; according to this embodiment, the engravings may be micro-circles situated on the nasal and the temporal side of the lens.
- the attitude of the lens to be tested is compared to the attitude of the defect free model lens and a metrics is applied to align both attitudes if they do not coincide.
- the model image of a reflected or transmitted image of the pattern on a defect free optical component is calculated theoretically by using the design of a model optical component.
- the model image of a reflected or transmitted image of the pattern on a defect free optical component is calculated on the basis of defect free optical component which have previously been observed and selected; according to this embodiment, engraving segments of the defect free optical component may be advantageously used, identified and replaced by an interpolated segment.
- an adaptive filtering is applied to the images in order to spare small defect zones and homogenise larger scale defect zones, when comparing phase and amplitude images of both optical component to be tested and defect free model optical component.
- a sensor dust filtering metrics is applied.
- defects are classified after separation of dust and noise in two types which are extended defects such as for example waves, polarized marks, varnish drops, conantric streaks and point defects such as for example craters, fibres, dirty inserts, handling scratches, black points, water marks.
- a decision step states whether the tested optical component is accepted or rejected.

The invention also relates to a device for implementing the preceding method and its different embodiments comprising means to generate a structured pattern, a screen, an optical component holder, a digital camera, image-processing means which comprise algorithms for phase extraction calculation, for conversion calculation, for derivation and/or integration calculation.

Means to generate a structured pattern and the screen may be included in the same apparatus, such as a video screen linked to a computer. The structured pattern may also be projected on a screen.

The structured pattern may be a continuously moving structured pattern or a step by step moving structured pattern.

The image-processing means may further include algorithms for B-spline interpolation calculation.

The invention also relates to a computer program product for a data processing device, the computer program product comprising a set of instructions which, when loaded into the data-processing device, causes the device to perform at least one of the steps of the preceding method and its different embodiments.

The invention also relates to the use of the preceding method and its different embodiments to apply a selection method to a set of optical components.

According to an embodiment the selection method is semi automatic and comprises firstly a visual test of a plurality of optical components done by an operator, where the operator selects a set of optical components which may be doubtful and where the preceding method and its different embodiments are applied to the set of the doubtful optical components.

For a better understanding, the invention and its further preferred embodiments will now be described, by way of non limiting examples, with reference to the following drawings in which.

Figure 1:
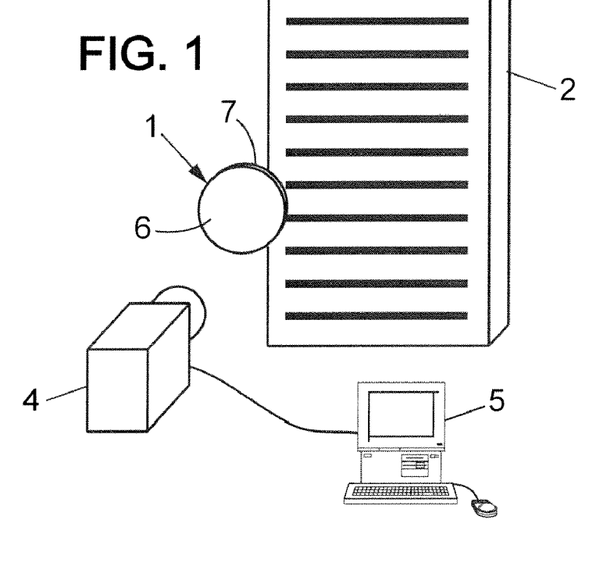
FIG. 1 is a schematic representation of a device used to implement deflectometry measurement.

FIG. 1 is a schematic representation of a device used to implement a deflectometry measurement using transmission of the light rays. A structured pattern is generated on a screen 2. A sample 1, such as a lens with a front surface 6 and a back surface 7, is placed so as to transmit the generated structured pattern. A camera 4 observes the sample 1 and acquires the transmitted image resulting from the distortion of the structured pattern through the sample 1. A computer 5 applies a metric to digitize the image and calculates the surface profile. The sample local slope map is the first derivative value of the profile surface, and the curvature is the secondary derivative value of the surface profile.

Following another embodiment, the device used to implement a deflectometry measurement according to the present invention is arranged so as to permit an image reflexion onto surfaces 6 and 7 of the sample 1, said reflected image being acquired by a camera.

The secondary derivative value of the surface is comparable to what the human eye actually sees.

Figure 2:
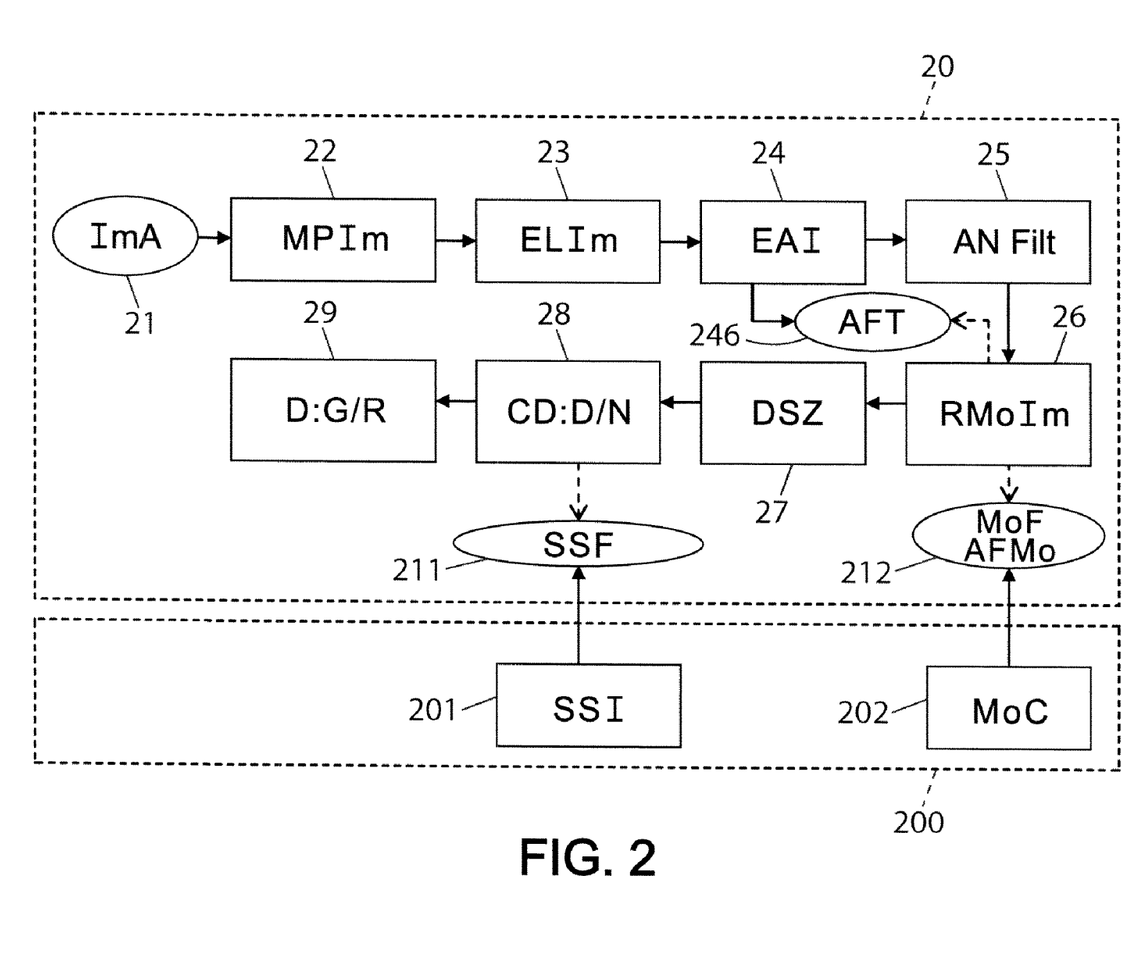
FIG. 2 is a general flow chart of a processing chain according to the invention.

FIG. 2 is a general flow chart of a processing chain according to the invention.

The image processing chain described here is part of the design of an automatic quality control system for ophthalmic lenses. The objective of this processing is the detection and location of different types of defects that can be detected from images formed by deflectometry and supplied by an acquisition system where phase and amplitude images are calculated.

The image processing chain can be used to test a plurality of optical components, namely lenses, of the same nominal reference. The nominal reference of the optical components is further referred as the "model". This image processing chain comprises two parts 20, 200 where first part 20 is dedicated to handle data related to a lens to be tested and part 200 provides to part 20 data related to the model and the sensor used.

In the present example, following steps of part 20 are implemented, where reference Im relates to the image of the lens to be tested and Mo relates to the model:

Im A 21: Image acquisition (either by transmission or reflection)
MPIm 22: Merging of phase images
ELIm 23: Extraction of the lens from the image
EAI 24: Extraction of attitude information
AN Filt 25: Adaptive noise filtering
Rmo Im 26: Realignment of model onto the image
DSZ 27: Detection of suspect zones
CD: D/N 28: Classification between defects and dust or noise
D: G/R 29: Decision: lens to be considered as good or rejected.

An attitude file of the tested lens AFT 246 is provided through the extraction of attitude information 24.

Two types of information are used in part 20 and provided by part 200.

MoF and AFMo, 212, are respectively data of surface profile, possibly with its derivatives, and data related to the attitude of the model.

SSF 211 is the sensor spot file including the characteristics of the sensor used to register the image during step 21.

Those information are calculated, separately from the lens testing part 20, in part 200 where:

SSI 201 relates to the sensor spot identification,
MoC 202 relates to the model creation.

As for an example the image acquisition step ImA 21 is performed thanks to an Ondulo device developed by Techlab SA and sold by Visuol Technologies (Metz-France) using phase shifting technique.

A structured light is displayed on a screen (not on the sample, as in a classical fringe projection system) and the camera observes the distorted reflected or transmitted image of the grid.

For each point (x, y) of the distorted image, the sinusoidal behaviour of light intensity is represented by the following equation:

$$I(x,y)=Io(x,y)\cdot[1+\emptyset(x,y)\cdot\cos(\Phi(x,y)+\Delta\Phi(x,y))]$$

Io: average local intensity
Ø: contrast of the fringes
Φ: phase of the considered point The geometrical configuration of the setup and the temporal phase shifting will make it possible to extract the phase variation $\Delta\Phi$, which is the variable to be determined for each point of the distorted image.

The light intensity equation has three unknown values, it is thus necessary to identify new equations to solve the problem. The "temporal" approach consists in evaluating these parameters for the same pixel onto the surface, but from several sequences during the shifting. To obtain this information, the displacement of the grid performed by the phase shifting is the most suitable and consists in measuring several intensities $I_k$, $k=0, 1, \ldots n-1$, separated by a constant phase variation $\delta$: $I_k = I(\Phi + k\delta)$.

The grid could be compared to a luminous ruler graduated with the known period p of its sinusoidal signal.

The phase $\Phi(x,y)$ represents the position on the grid plane and varies linearly with a rate of $2\pi$ per p. The phase shifting will detect exactly, usually $\frac{1}{200}^{th}$ of the grid period, the location of the light source points onto the grid. So, detecting the phase variation $\Delta\Phi(x,y)$ is equivalent to detecting the coordinates and the displacement $\Delta u$ of the source point.

As for an example, the case of a deflectometry measurement using reflexion is detailed, where a small variation of the local slope $\Delta\alpha$ will modify the angle of the reflected ray by $2\Delta\alpha$ and the position of the source point by $\Delta u$ onto the grid. Then, the phase variation $\Delta\Phi$ corresponding to the displacement $\Delta u$ is such that:

$$\Delta\Phi = 2 \cdot \pi u / p$$

The slope variation $\Delta\alpha$ is given by the relation:

$$2\Delta\alpha = 2 \cdot d(\Delta z)/dx = \Delta u / M(x).$$

To quantify the curvature variation between two points M and N, the equation $\Delta\alpha = s(x) \cdot \Delta\Phi(x)$, where the coefficient $s(x) = p/4\pi M(x)$ is the measurement sensitivity, clearly completes the relation between the phase shifting and the slope variation. Then, the characterization of the curvature variation between M and N is obviously obtained by derivation of the slope variation.

Due to the process by which they are formed, the images supplied by Ondulo using either reflected or transmitted images are contaminated with a lot of noise, which makes the detection of excessively small defects difficult. In addition, the variety of types of defects to be detected (HF and BF defects) makes it very difficult to use "simple" methods based on measurements made in sliding windows and not using any a priori knowledge of the inspected lens. This approach leads to a multiplication of the number of processes to be performed (one per defect type), and so to a high algorithm cost and complex system configuration in view of the number of thresholds to be set.

The strategy proposed in the present invention uses a general formalism suitable for all defects that can be detected from the images supplied (a single process for all defects). The approach consists of creating a model image for a good lens of each dioptre power. When a lens must be tested, it is then compared to an associated good lens model: It is declared defective if a zone in it is too far from the profile of the model. This method is generic for any defect type, and the laborious calculation of the model itself is performed outside production and reduces algorithm cost for each lens testing. In addition the images supplied are merged to form only one, which then serves as the basis for all the processing.

So as to completely reconstruct the observed lens, the images with vertical curvature $I_v$ and horizontal curvature $I_h$ supplied by the Ondulo system are merged in step MPIm 22. Each point is here seen as a 2 component vector (one per curvature direction). The value carried into the reconstructed image $I_r$ for the point $p_j$ is obtained by calculating the norm of its associated vector, using the formula:

$$I_r(p_j) = \sqrt{I_h(p_j)^2 + I_v(p_j)^2}$$

Merging is performed from the vertical curvature image and the horizontal curvature image, both of the same size. The result of the merging consists of an image of the same size as the input images.

The lens is then extracted from the image in step ELIm 23. The objective of this function is to keep only the useful part of the information contained in the image (i.e. the information related to the lens). The hypothesis that the centre of the image is situated inside the closed surface relative to the lens is made. An increase in the region is performed around this point by a recursive algorithm. The stop criterion is then the meeting of the characteristic values of a contour.

The extraction of the lens is for example done from an image in .RES format provided by the Ondulo system.

The result of the extraction is an image whose dimensions remain unchanged from their starting values.

It could also be possible to seek a lens contour point in several a priori reliable zones, and connecting the points detected by straight line segments using lens contour polygonisation technique.

When the lenses to be tested are progressive addition lenses, PAL, a further step, EAI 24, is preferably used where the extraction of attitude (orientation) information is performed. This step is advantageous for PAL testing because PAL are not symmetric lenses and comprises at least one surface with far, intermediate and near vision zones and thus have an asymmetric profile. The reflected or transmitted image is thus dependant on the PAL orientation.

A solution to test PAL is to orientate them before recording the reflected or transmitted image of the structured pattern. Such a solution needs a previous step and may be time consuming and/or costly.

A preferred solution is to use specific characteristics of PAL in the image processing chain. Therefore a proposed solution is to extract attitude information from the reflected or transmitted image of the PAL to be tested an to reconstruct the image in a given orientation.

The inventors have found that the engravings on PAL are of great interest to extract attitude information.

Figure 3:
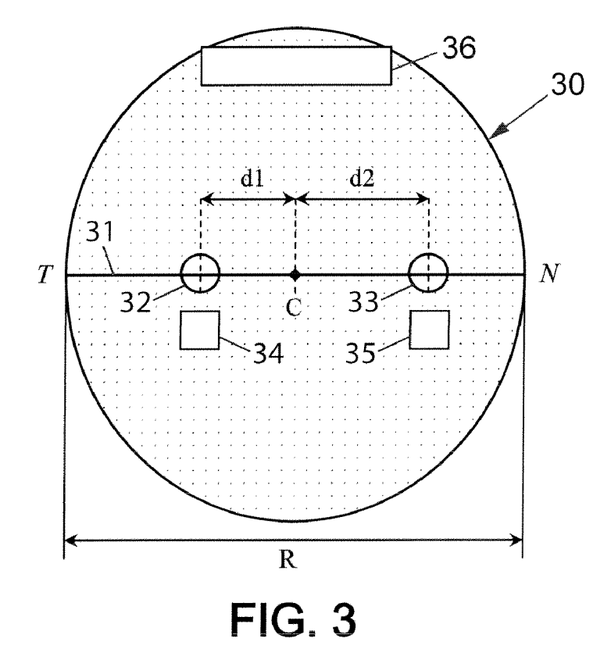
FIG. 3 is a schematic view of a front surface of a progressive addition lens.

FIG. 3 shows a PAL front surface 30 with its engraving zones. PAL engraving zones are defined for example in ISO standard n°8980-2, paragraph 7, and permanent marking, i.e. engravings, includes at least the alignment reference markings comprising two marks 32, 33 located 34 mm apart, equidistant to a vertical plane through the fitting point or prism reference point, indication of the addition power, indication of the manufacturer or supplier.

As for an example, the PAL surface 30 of FIG. 3 comprises two micro circles 32, 33, where the micro circle 32 named MCT is located on the temporal side T of the PAL and the micro circle 33 named MCN is located on the nasal side N of the PAL. The horizontal line 31 passes through the geometric centre C of the PAL. Characters are engraved in zones 34 named ST and 35 named SN situated under line 31 and respectively under micro circles 32 and 33. A serial number is engraved in zone 36 situated at the top of the PAL.

Based on these PAL characteristics, the extraction of information on the lens dimensions and its attitude is made at the time of acquisition. The location of certain support points will serve to realign the model to the image of the lens to be tested. The procedure is automatic and is as follows:

The first stage consists of searching for occurrences in the image of a previously learned pattern (such as a micro-circle MCT or MCN present in the PAL). Only the best occurrence is selected, meaning that one giving the maximum correlation score with the learned pattern. As, there are exactly 2 micro-circles present on each progressive lens, a nasal and a temporal, the second step consists of identifying which of these micro-circles has been detected (MCN or MCT). To remove this ambiguity, one can use the fact that the distances separating each of the micro-circles from the geometric centre of the lens C is characteristic are known for a given set of PAL (as for an example d1=14 mm, d2=20 mm, R=80 mm).

Let d be the distance between the micro-circle detected and the geometric centre of the lens: if the ratio $$\frac{d}{R}$$

is closer to $$\frac{d1}{R}$$

than to $$\frac{d2}{R},$$

the micro-circle detected is MCT, if not it is MCN.

From this information, the other engravings present in the image may be extracted. For a progressive lens, the set of engravings which can be advantageously extracted following:

The temporal micro circle MCT 32
The characters present under MCT (ST) 34
The nasal micro circle MCN 33
The characters present under MCN (SN) 35
The sequence of characters present on the edge of the lens (SERIAL) 36

Figure 4:
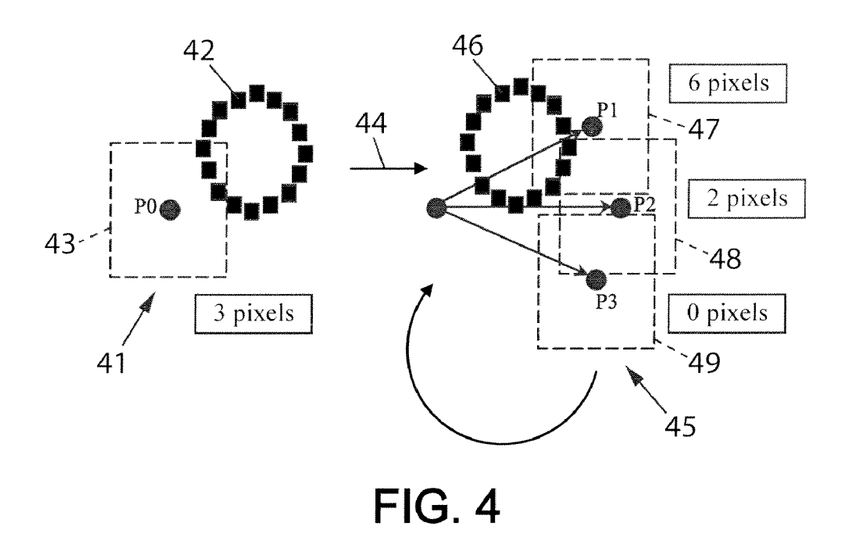
FIG. 4 is a schematic sketch of a principle used to handle the attitude parameter.

Following steps can be used for attitude extraction: The image is first binarised into two classes: an "engraving" class and a "lens" class. A pixel is classified as "engraving" if its grey level is greater than a high threshold or less than a low threshold. From the detected micro-circle, the a priori positions in the image of the other engravings are deduced (These a priori are entered "permanently" in the algorithm). In addition each engraving type is associated with a predefined fixed size mask. A descent process is then started around each a priori position: the mask associated with the current engraving is translated into x and y so as to maximise the number of pixels labelled "engraving" that it covers. This principle is illustrated in FIG. 4.

After identification of a micro circle 42 position in the image 41 the process is initialized in an a priori initial position P0 situated in zone 43.

Transformation 44 is thus applied where a mask 46 is translated in different positions P1, P2, P3 in respectively zones 47, 48, 49 to form a new image 45. The number of "engraving" pixels is determined in each zone. In the present example, zone 41 comprises 3 pixels, zone 47 comprises 6 pixels, zone 48 comprises 2 pixels, zone 49 does not comprise any pixel. The new position for iteration is thus P1 and the iteration process is done up to optimization of the pixel number.

The image coordinates of the lens geometric centre, and all the coordinates of any engravings present may then be saved in a text file.

An input image where the lens has been extracted from the background and an MIL file containing a pattern learned can be provided.

The output data resulting from this step is a text file including all the points of interest and information extracted.

Figure 5:
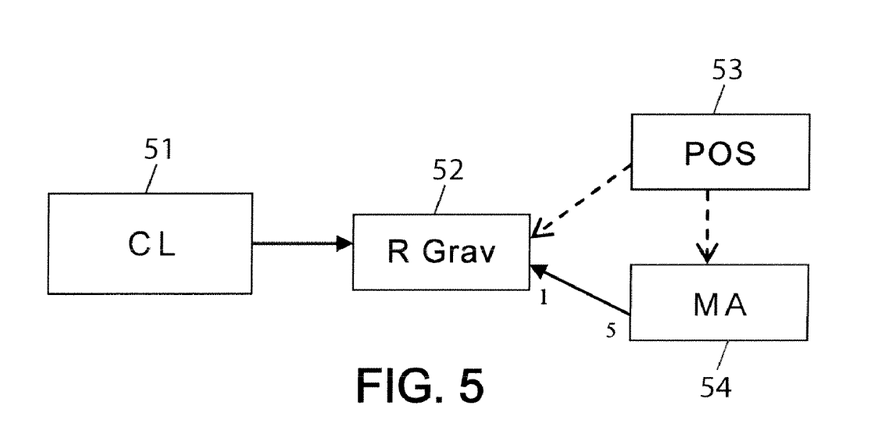
FIG. 5 is a class diagram directed to an embodiment to handle the attitude parameter.

FIG. 5 illustrates corresponding class diagram where CL 51 is the client, R Gray 52 is the engraving search, POS 53 is the position, MA 54 is the mask.

The generated attitude information file AFT 246 of the sample to be tested is then stored.

A step 25 in FIG. 2, AN Filt, can then be performed where the image of the lens to be tested is subject to an adoptive filtering.

So as to limit the influence of noise in the detection of defects, an adaptive filtering is performed whose aim is to spare the small defect zones (Black points, blisters) and to homogenise the larger scale structures (Waves).

The filter equation employed is as follows:

$$F'(p_j) = \frac{\sum_{i \in V} F(p_i) \cdot ((K\gamma \|p_j p_i\|)^4 + 1)^{-1}}{\sum_{i \in V} ((K\gamma \|p_j p_i\|)^4 + 1)^{-1}}$$

With:
F is the table of values representing the initial image
F' is the table of values representing the image after filtering
V is the neighbourhood of the points (Meaning the set of $p_i$) around the point $p_j$
K is the filter strength. The smaller K is and the more the filter smoothes the image in a significant way.
$\gamma$ is the ratio of the mean to standard deviation of the points in V.

The filter behaviour is thus as follows:
There are two weighting levels. A first level that takes into account the spatial arrangement of the points: The closer a point is spatially to $p_j$, the higher its weight in the result (based on classical linear Gaussian filtering). The second level takes account of the disparity in grey levels in the defined neighbourhood: The more homogenous the grey levels in V (i.e. large $\gamma$), the greater the smoothing in the zone, and conversely.

The filtering parameters are: an image to be filtered, a value for K and a neighbourhood size.

The filtering result is then an image with more or less smoothed zones.

Another filtering method could use the fact that the noise frequency is high compared to the frequency of the signal of interest, and a Fourier spatial filtering could be used. The influence of lens dioptre power and the acquisition parameters (Size of fringes) on the noise frequency would then advantageously be studied so as to eliminate it as well as possible.

Following step according to FIG. 2 is realignment of the model onto the image RMoIm 26. As this step uses the data files related to the model, MoF and AFMo in case of PAL, the model creation step MoC 202 will be now described.

The objective here is to create a perfect lens profile (for a given dioptre value) allowing easy subsequent identification of the defect zones in a lens to be tested by simple comparison. The objective is thus to subtract all the high frequency noise, from various sources (Ondulo measurement noise . . . ) from the "true" low frequency signal corresponding to the lens profile. Ideally, this would be obtained by averaging N good lenses (N as large as possible).

Preferably the model is created from a minimum number of lenses, and obtained by iteration of large size spatial filters (mean and median) applied to the image of a good lens. The mean profile thus obtained is then regularly sampled: This defines a set of check points. An interpolation function then allows the restitution of the intermediate points between two adjacent check points.

A polynomial interpolation method such as B-splines can be used. Their special characteristic is that, for a degree at least equal to 2, the resulting curve is continuous and differentiable at all points (Slope conserved around the check points). Such a property is useful for the modelling of ophthalmic lens profiles. Different polynomial orders have been tested and an order 2 polynomial appears to be sufficient to interpolate the profile between 2 check points.

The procedure uses is as follows: for each line and each column, a set of points distributed as regularly as possible is selected, known as the "check point set". The interpolation using 3-splines between 2 successive check points is then calculated. The interpolation calculation is performed 4 times in all:

First for the lines in the forward direction (From left to right)

Secondly for the lines in the reverse direction (From right to left)

Thirdly for the columns in the downward direction (From Top to Bottom)

Fourthly for the columns in the reverse direction (From Bottom to Top)

The final model is then the mean of these 4 interpolations.

With all the calculations done, the equations in the 1D (line or column) profile model are as follows:

Let $\{p_i, i \in [1,n]\}$ be the set of check points and $Q_i(t)$ the interpolated value at the position $t \in [0; 1]$ between the check points $p_i$ and $p_{i+1}$. Following equation is obtained:

$$Q_i(t) = B_0(t)P_i + B_1(t)P_{i+1} + B_2(t)P_{i+2}$$

With:

$$B_0(t) = \frac{1}{2}(1 - 2t + t^2)$$

$$B_1(t) = \frac{1}{2}(1 + 2t + t^2)$$

$$B_2(t) = \frac{1}{2}t^2$$

However, in present case the B-spline curve will not be closed (No looping between the first check point and the last along a line or column). Connection conditions are thus introduced at each end.

Thus, if i=1, $B_i$ is replaced by the following function $A_i$:

$$A_0(t) = 1 - 2t + t^2$$

$$A_1(t) = \frac{1}{2}(-3t^2 - 4t)$$

$$A_2(t) = \frac{1}{2}t^2$$

And if i=n, we replace $B_i$ by the following function $C_i$:

$$C_0(t) = A_2(1-t)$$

$$C_1(t) = A_1(1-t)$$

$$C_2(t) = A_0(1-t)$$

When sampling a line or column of check points, a problem can happen with progressive lenses due to the presence of engravings that do not have to be taken into account in the profile calculation. Thus, with regular sampling, if a check point is situated in an engraved region, this may seriously perturb the profile obtained. To overcome this problem, a further step is proposed and illustrated in FIGS. 6 and 7.

Figure 6A:
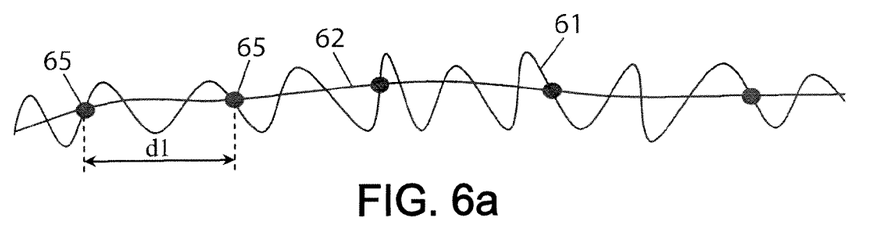
FIG. 6a to c are schematic sketches related to data treatments.
Figure 6B:
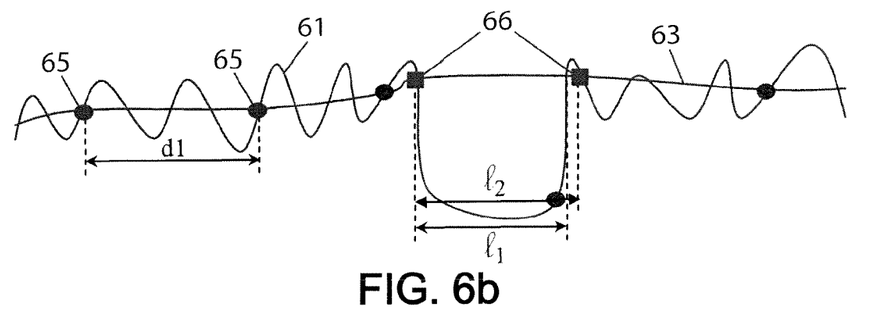
Figure 6C:
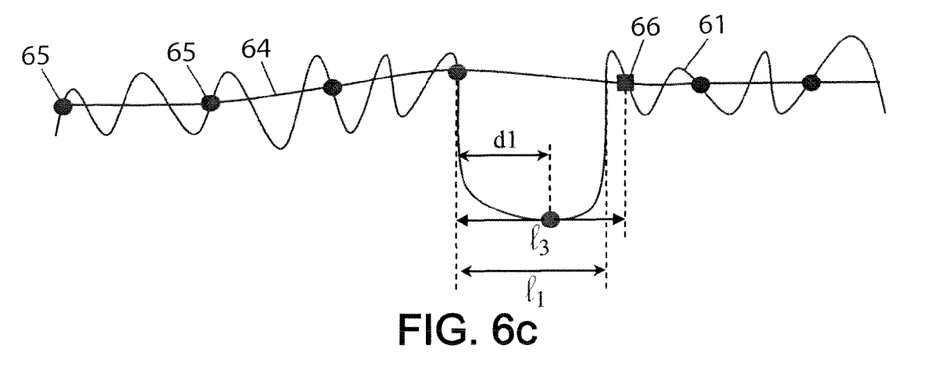

FIG. 6 shows three different profiles where in FIG. 6a no "engraving" zone is met and where an "engraving" zone is met in FIG. 6b and c.

Line 61 results from measurement and line 62 to 64 are the profiles obtained after the present step. Points 65 are check points. The distance between two check points is d1.

If in the length of the structure to be modelled no check point corresponds to an "engraving" pixel, then all the check points are regularly distributed.

If in the length of the linear structure there is an "engraving" segment which width is 11 and a check point is included in this segment, then the procedures for replacing this check point are following:

If the ends of the "engraving" segment do not correspond to any already existing check point, then the invalid check point within 11 is replaced by these two ends as shown on FIG. 6b, where replaced points are squares 66. The distance between the two successive points is then 12.

If one of the ends of the "engraving" segment corresponds to an already existing check point within 11, then the invalid check point is replaced by the end that is not already referenced as shown on FIG. 6c where replaced point is square 66. The distance between the two successive points is then 13.

The input parameters are: a horizontal curvature image, a vertical curvature image, a neighbourhood size and an iteration number.

The output data is for example an image file in Ondulo format (.RES) and a text file containing the extracted information on the model attitude.

Figure 7:
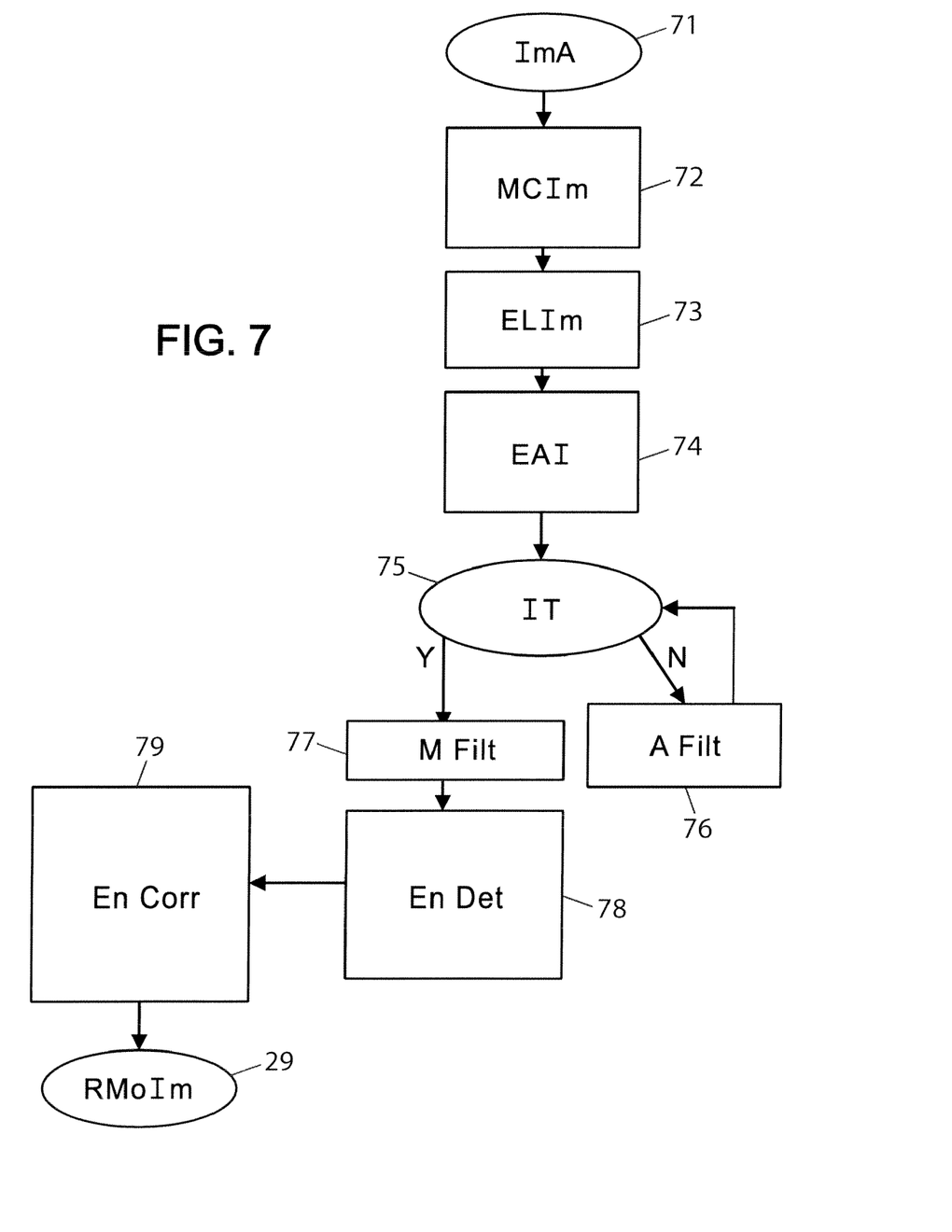
FIG. 7 is a flow chart of part of a processing chain according to an embodiment of the invention.

FIG. 7 shows the flow chart of this step where:

ImA 71 corresponds to Image acquisition

MCIm 72 corresponds to curvature image merging

ELIm 73 corresponds to lens extraction

EAI 74 corresponds to attitude information extraction

IT 75 corresponds to the iteration process

Y to Yes and N to No

A Filt 76 corresponds to an averaging filter

M Filt 77 corresponds to a median filter

En Det 72 corresponds to detection, sampling to take into account engravings,

En Corr 79 corresponds to engraving correction, interpolation by B-spline (forward line, reverse line, down column, reverse column), RMoIm 29 is the realignment step of the model onto the image shown on FIG. 2.

It would also be possible to complete mathematical modelling of the deflectometer system responses in accordance with the acquisition parameters and the lens dioptre value.

From the lens type to be tested it would then be possible to calculate the corresponding usable theoretical model for the identification of the suspect zones.

The RMoIm 29 realignment of model to the lens to be tested image is now described. This step comprises the determination of all the translation, rotation and scale factor parameters to be applied to each point of the model to achieve the best superposition of the image and test lens. From then, the model and test lens will have similar attitudes. To do this pairs of points of interest are previously extracted. The transformation parameters estimated from these pairs are then applied to each point of the model.

Let $P(X_i, Y^i)$ be a point of interest in the image of the test lens and $p(x_i, y_i)$ a point of interest in the model, both expressed in the same coordinate system. Aligning the pair p on P comes down to performing the following transformation:

$$\begin{bmatrix} X_i \\ Y_i \\ 1 \end{bmatrix} = \begin{bmatrix} \lambda_x\cos(\theta) & -\lambda_x\sin(\theta) & t_x \\ \lambda_y\sin(\theta) & \lambda_y\cos(\theta) & t_y \\ 0 & 0 & 1 \end{bmatrix} \cdot \begin{bmatrix} x_i \\ y_i \\ 1 \end{bmatrix}$$

where, $t_x$, $t_y$ represent the translations in x and y, $\lambda_x$, $\lambda_y$ the scale factors in x and y and $\theta$ the rotation about the axis Oz respectively. Determining all these 5 parameters thus requires at least 3 pairs of points of interest and the solution of non linear system.

Given that the acquisition conditions are sensibly identical for all the images, translations and scale factor corrections will be small. A faster and simpler realignment procedure is thus employed.

A translation in x and y, a rotation about the axis Oz, and a scale factor correction in x and y are made sequentially. The translation applied corresponds to superposing the centre of the model on that of the lens to be tested.

For the progressive lens case a rotation angle is calculated based on the prior detection of micro-circles.

Using the notation of FIG. 3, the direction vectors of the straight lines linking the geometric centre of a lens to each micro-circle (MCT 32 or MCN 33) are calculated: Let $\vec{v_{t1}}$ and $\vec{v_{t2}}$ be these vectors. The same is done for the model: Let $\vec{v_{m1}}$ and $\vec{v_{m2}}$.

The following angles are then defined:

$$\theta_{MCN}=(\vec{v_{t1}},\vec{v_{m1}}) \text{ and } \theta_{MCT}=(\vec{v_{t2}},\vec{v_{m2}})$$

The rotation angle is then chosen as being the mean of these 2 angles (Limitations of calculated angle errors for each micro circle):

$$\theta = \frac{\theta_{MCN} + \theta_{MCT}}{2}$$

The calculation of new coordinates for the model points is done for example by a MIL library commercialized by the company Matrox.

Figure 8:
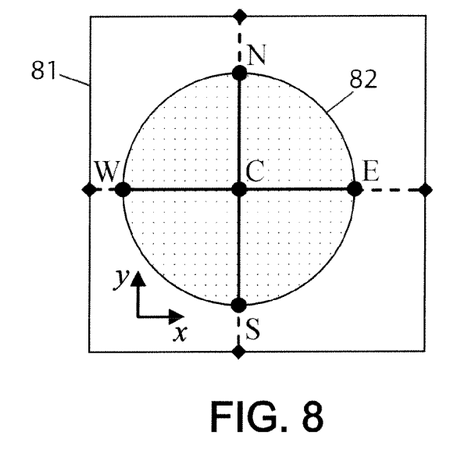
FIG. 8 is a cardinal diagram of an image of a lens to be tested.

For the scale factor correction, the 4 cardinal points (N, S, E, W) are first calculated on the contour of the model and the lens to be tested (See figure below. This extraction is done using the same procedure as that providing the extraction of attitude information, with the exception that here the starting point is no longer the centre of the lens or model, but each of its orthogonal projections on the edges of the image (Represented by the square points on the figure). The 4 cardinal points are then situated on the edges of the lens (Represented by circular points in the figure). We then form the hypothesis that the scale factors in x and y are constant throughout the image (But not necessarily equal: the lens can then be elliptical, with its two axes being horizontal and vertical). The scale factors denoted by $\lambda_x$ and $\lambda_y$ are then obtained as below:

Let (N, S, E, W) be the cardinal points as shown on FIG. 8 in the image of the lens 82 to be tested and C the centre of the lens. Let (N', S', E', W') and C' be their equivalents in the model. Equations are then following:

$$N_y-C_y=\lambda_y\cdot(N'_y-C'_y) \text{ and } S_y-C_y=\lambda_y\cdot(S'_y-C'_y)$$

$$O_x-C_x=\lambda_x\cdot(O'_x-C'_x) \text{ and } E_x-C_x=\lambda_x\cdot(E'_x-C'_x)$$

and, averaging on either side of the centre:

$$\lambda_x = \frac{1}{2}\left(\frac{O_x-C_x}{O'_x-C'_x} + \frac{E_x-C_x}{E'_x-C'_x}\right)$$

$$\lambda_y = \frac{1}{2}\left(\frac{N_y-C_y}{N'_y-C'_y} + \frac{S_y-C_y}{S'_y-C'_y}\right)$$

It is then possible to avoid calculating the new coordinate from a model point after this transformation and to work from the input image space: at a given input point, the coordinates in the input image space are deduced using the inverse transformation and associated value are obtained by bilinear interpolation.

Input data for this step are test lens image from which it has been previously extracted, associated model, information on the respective attitudes of the test lens and the model.

The model is then readjusted onto the lens to be tested.

Figure 9:
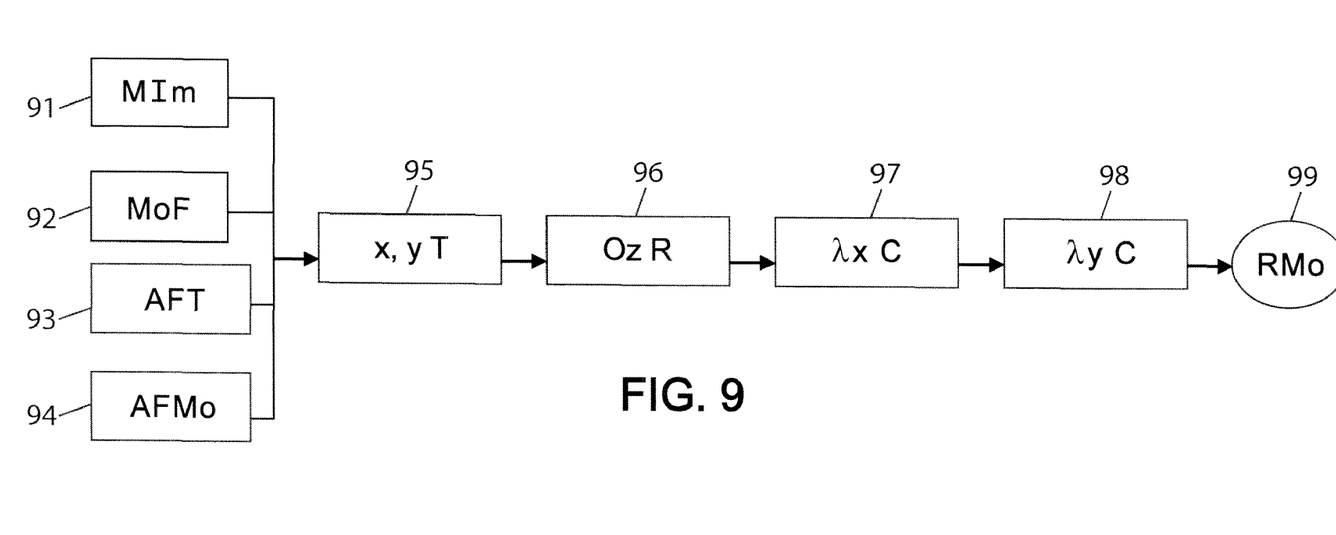
FIGS. 9 and 10 are flow charts of part of a processing chain according to embodiments of the invention.

FIG. 9 shows a flow chart of this step where

MIm 91 corresponds to the merged image of the lens to be tested

MoF 92 corresponds to the image file of the model AFT 93 corresponds to the attitude of the lens to be tested AFMo 94 corresponds to the attitude of the model x, yT 95 corresponds to the translation calculation OzR 96 corresponds to the rotation calculation λxC 97 corresponds to the λx calculation λyC 98 corresponds to the λy calculation RMo 99 corresponds to the realigned model Detection of suspect zones corresponding to step DSZ 27 of FIG. 2 will now be described.

The objective here is to detect the zones suspected of being defect zones from the adjusted model and the filtered image of the test lens. From the parameters describing the model at each point and by comparing with the value at the same point in the test lens image, it will be decided whether the point is suspect or not.

If the following criterion is verified, then the point is not considered as suspect:

$$|M(p_j)-F(p_j)|\leq K(p_j)$$

Where K sets the maximum tolerance related to the model-measured value difference. This tolerance varies with the local phase slopes in the model in accordance with the following formula:

$$K(p_j) = \alpha\left(1 + \beta\frac{\arctan\left(\frac{max-min}{V}\right)}{\pi/2}\right)$$

Where max represents the maximum grey level encountered in the neighbourhood of $p_j$, min the minimum value encountered, V the neighbourhood size, α the required tolerance factor, and β a positive integer.

Thus when the slope in the model is very small (Lens centre), the tolerance K is close to α, and when the slope is high (Lens edge) this tolerance then tends to $(1+\beta)\alpha$. This function K then allows us to have an adaptive tolerance depending on the position studied in the lens. This avoids classifying the whole edge of the lens as a suspect zone due to measurement or alignment uncertainties.

The adjustment of β sets the difference in processing between the centre and the edge of the lens.

For progressive lenses, the engraving zones located on the lens to be tested are not taken into account. This means that no defect of any type will be detect in these zones.

The input data are the realigned model and the filtered image of the lens to be tested.

The output data is a ternary image: A black point corresponding for example to a point that is faithful to the model, a grey point corresponding for example to a suspect point departing from the model to a certain extent, a white point corresponding for example to a point judged very suspect because it differs from the model by more than a certain amount.

Filtering of dust on the sensor corresponding to steps SSI 201 and SSF 211 of FIG. 2 will now be described.

The objective here is to eliminate the dust resting on the lens image sensor. Since this dust is on the sensor, it is not subject to the optical deformation due to the lens: It is thus always in the same position in the image, whatever the lens dioptre power.

An empty image (without lens) is taken. The phase image obtained will thus be that of the screen, which can be compared to a flat surface. It is thus legitimate to approximate this surface by a plane. The calculated plane is thus the optimum plane in the least squares sense, of the form:

$$z = a \cdot x + b \cdot y + c, \text{ with } a, b, c \text{ the plane parameters}$$

After applying several low pass filter (Mean, median) iterations, the planar model of the image is calculated as follows: Let $\{(x_i, y_i, z_i), i \in [1; N]\}$ be the set of data points making up the phase image.

With all calculations done, the parameters of the optimum plane in the least squares sense are obtained by calculating the following parameter vector:

$$\begin{bmatrix} a \\ b \\ c \end{bmatrix} = \begin{bmatrix} \sum_i x_i^2 & \sum_i x_i y_i & \sum_i x_i \\ \sum_i x_i y_i & \sum_i y_i^2 & \sum_i y_i \\ \sum_i x_i & \sum_i y_i & N \end{bmatrix} \cdot \begin{bmatrix} \sum_i x_i z_i \\ \sum_i y_i z_i \\ \sum_i z_i \end{bmatrix}$$

Once the planar model has been calculated, the image is compared to this model for a low tolerance threshold in accordance with the defined procedure. Thus all the points that are too far from the model are detected throughout the image and identified as "Sensor" spots.

The input parameters are for example an image in "res" format taken empty, a tolerance threshold.

The output data is for example a text file listing each point making up a "sensor spot".

Figure 10:
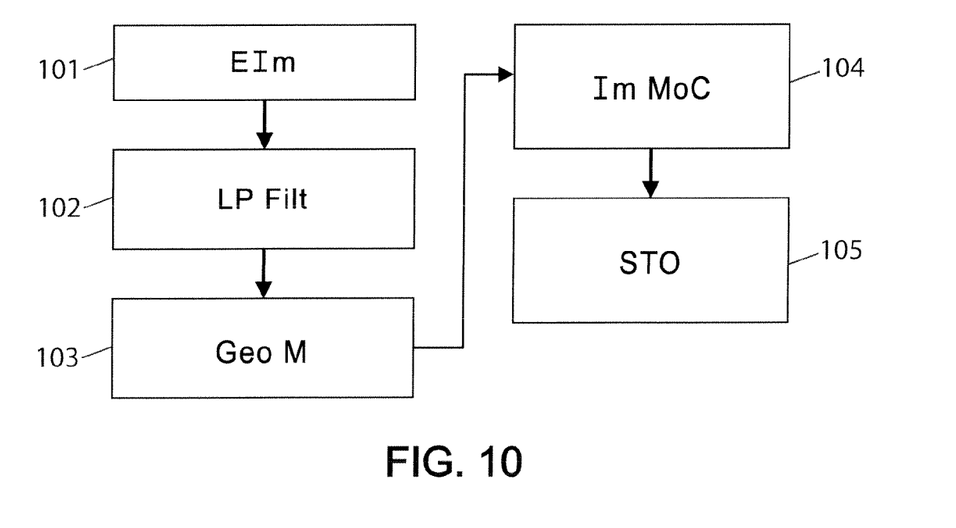

FIG. 10 is a flow chart of this step where:

Elm 101 corresponds to acquisition of an empty image

LP Filt 102 corresponds to applying low pass filtering (averaging, median)

GeoM 103 corresponds to geometric modelling

ImMoC 104 corresponds to image/model comparison

STO 105 corresponds to storage of detected points in a text file.

Classification of suspect zones as defect or dust/noise corresponding to step CD:D/N 28 of FIG. 2 will now be described.

Given the panel of defects to be detected, these have been separated into two classes: Defects referred to as "extended" and defects referred to as "points". They are divided as shown in table 1:

TABLE 1

| Extended defects | Point defects |
| --- | --- |
| Waves | Craters |
| Polarised marks | Fibres |
| Varnish drops | Dirty insert |
| Concentric streaks | Handling scratches |
|  | Black points |
|  | Water marks |

Each of these classes is associated with specific processing.

The processing of extended defects comprises a morphological closure to agglomerate small suspect regions close to each other thus forming a single large suspect region. Each identified suspect region is added to a list of suspect regions. This structure allows the creation of a region graph that may be useful if the complexity of the mark continues to increase. This list is then filtered so as to retain only those that have a minimum size.

The processing of point defects is as follows: Each suspect region is added to a list of regions, filtering is performed on this list so as to eliminate very small regions due to Ondulo measurement noise, and lastly a final filtering allows the number of dust particles interpreted as point defects to be limited. This filtering proceeds as follows and as illustrated on FIGS. 11a to 11d.

Figure 11A:
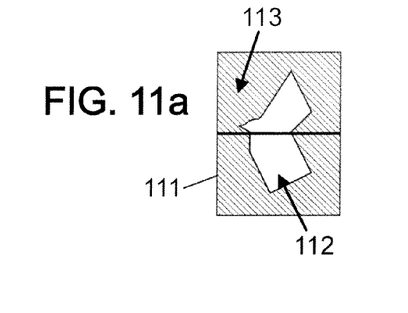
FIGS. 11a to 11d relates to a defect classification step according to the invention.

FIG. 11a shows an image 111 comprising a suspect zone 112 and its neighbourhood 113.

Let $M_z$ be the maximum value over a suspect zone 112, $m_z$ the minimum and $\mu_v$ the mean of the values in the neighbourhood 113 of 112.

Figure 11B:
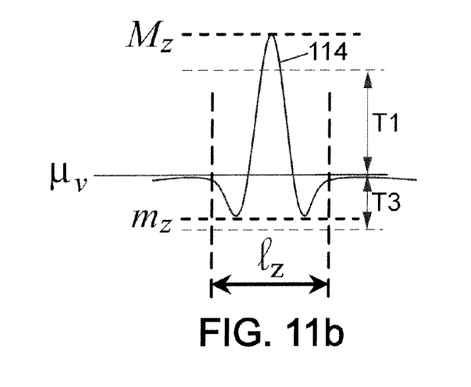
Figure 11C:
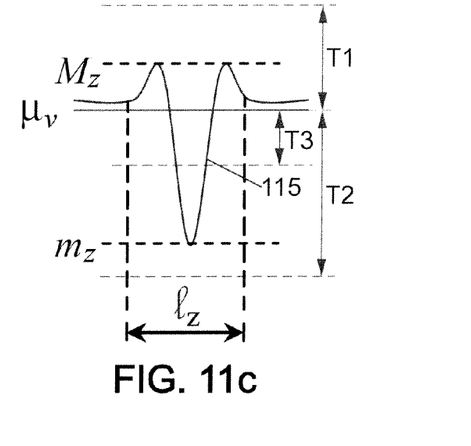
Figure 11D:
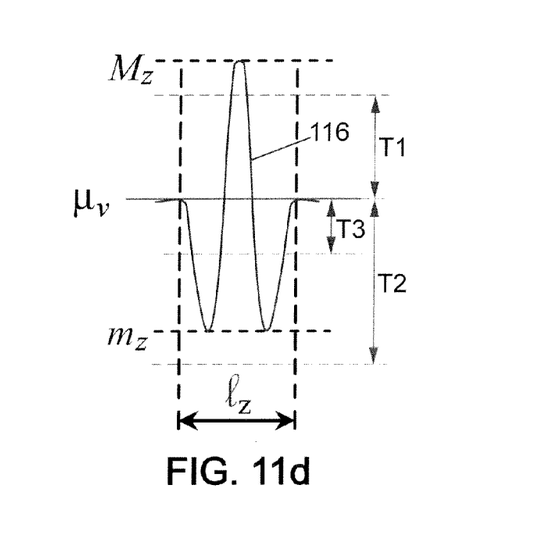

FIGS. 11b, c and d show three suspect zones values 114, 115, 116 where lz is the width of the suspect zones.

To discriminate an unwanted dust signature from a defect zone sought for point defect, the following two values are calculated:

$$A_1 = M_z - \mu_v, \text{ and } A_2 = \mu_v - m_z$$

According to an embodiment, the values $A_1$ and $A_2$ are compared to threshold values:

a first filtering criterion has been identified by the inventors: if $A_1$ is less than a given threshold value $T_1$, then the suspect zone is described as dust and eliminated. The curve 115 of FIG. 11c illustrates such a case.

a second filtering criterion has been identified by the inventors: if $A_1$ is more than $T_1$ and if $A_2$ is more than another threshold value $T_3$ and less than another threshold value $T_2$, then the suspect zone is described as dust and eliminated. The curve 116 of FIG. 11d illustrates such a case.

According to an improved embodiment of the second filtering criterion, the data related to the zone to be discriminated are considered at the value $T_3$. The number of pixels at $T_3$ are determined in order to calculate the surface, S, of the peak at $T_3$. A threshold criterion can be applied to enhance the dust filtering capacity, where a dust is identified if S is also less than a threshold surface value $S_{min}$.

According to a further embodiment of the dust filtering step, the maximum value, $M_z$, over a suspect zone 112 has also to be less than a saturation value $Sat_{max}$.

The input parameters are: the threshold values which allow discrimination between dust and a point defect, the size of the structuring element and the minimum size to be reached for an extended defect, as well as a file listing all the sensor spots.

If the here above mentioned criteria are fulfilled, the suspect zone is eliminated. If not, it is classified as a point defect.

An example of a point defect signature is illustrated on the curve 114 of FIG. 11b, where $M_z$ is more than $T_1$ and $m_z$ is less than $T_3$.

According to an example of the filtering method, following threshold values have been determined for pixels data between 0 and 255 grey level:
$T_1$=60 (grey level)
$T_2$=90 (grey level)
$T_3$=25 (grey level)
$Sat_{max}$=230 (grey level)
$S_{min}$=0.02 mm²

Resulting output data can be a list including all regions considered as defect zones.

Figure 12:
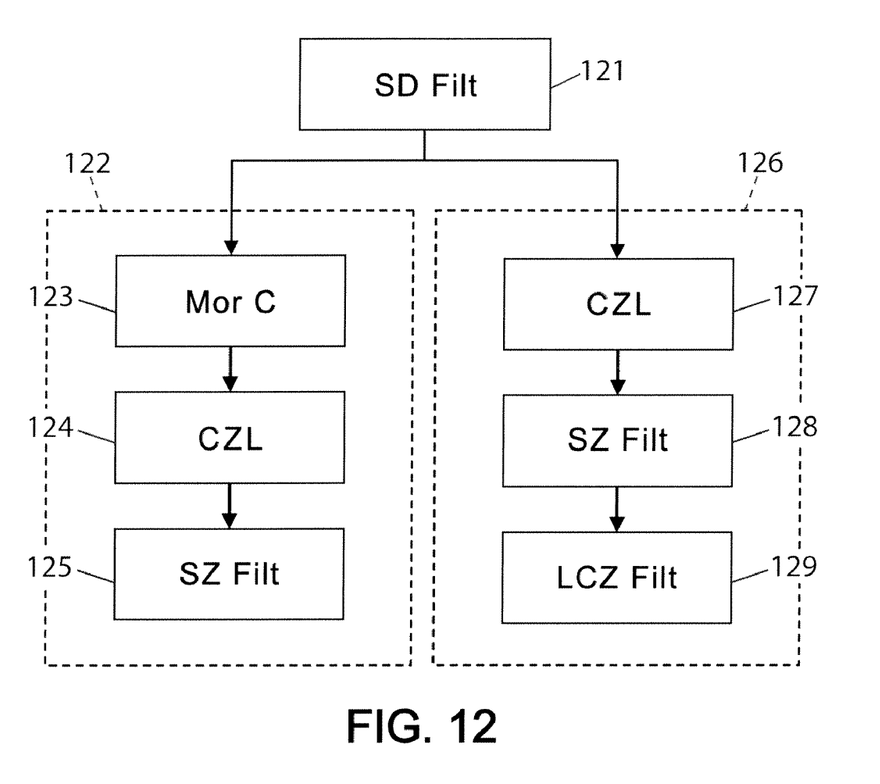
FIG. 12 is a flow chart of part of a processing chain according to an embodiment of the invention.
Figure 13:
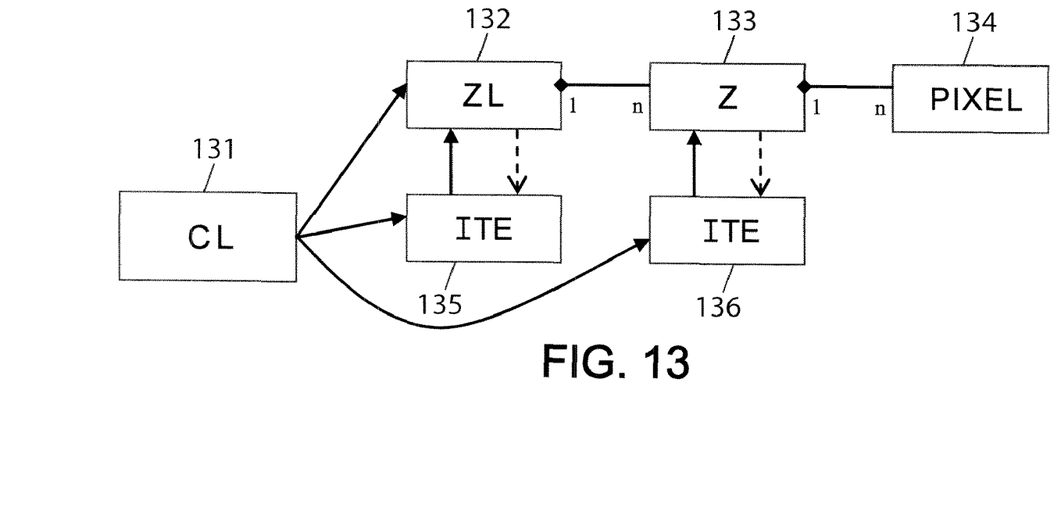
FIG. 13 is a class diagram directed to an embodiment for defect classification.

FIG. 12 shows a flow chart of the present step where:
SD Filt 121 corresponds to filtering dust from the sensor
122 corresponds to processing for extended defects
126 corresponds to processing for point defects
MorC 123 corresponds to morphological closure
CZL 124 corresponds to creation of a list of connected zones
SZ Filt 125 corresponds to small zone filtering
CZL 127 corresponds to creation of a list of connected zones
SZ Filt 128 corresponds to small zone filtering
LCZ Filt 129 corresponds to low contrast zone filtering
FIG. 13 shows corresponding class diagram where:
CL 131 corresponds to the client
ZL 132 corresponds to the list zone
Z 133 corresponds to the zone
PIXEL 134 corresponds to the pixel
ITE 135 corresponds to an iterator
ITE 136 corresponds to an iterator The last step D: G/R 29 of FIG. 2 is then implemented, based on resulting data from previous step and threshold values to decide if the tested lens is accepted or has to be rejected.

While the present invention has been described by way of illustration of its preferred embodiments, it will be understood that the invention is not limited to them and may be carried into practice by persons skilled in the art with many variations, modifications and adaptations, without departing from its spirit or exceeding the scope of the claims.

The invention claimed is:

1. A method for detecting defects in an optical component to be tested, such as a lens, comprising the steps of:
providing a structured pattern;
recording the reflected or transmitted image of the pattern on the optical component to be tested;
phase shifting the pattern and recording again similarly the reflected or transmitted image;
calculating the local phase and amplitude images of the optical component to be tested;
calculating a model image of a defect free optical component and determining corresponding phase and amplitude images of the defect free model optical component;
comparing phase and amplitude images of both optical component to be tested and defect free model optical component;
determining suspect zones in the optical component to be tested; and
applying a metrics to separate dust and noise from other defects;
wherein the metrics compare the values of $A_1=M_z-\mu_v$ and $A_2=\mu_v-m_z$ with threshold values so as to separate dust from other defects, $M_z$ being the maximum value, $m_z$ the minimum value and $\mu_v$ the mean of the values of the phase or amplitude over a suspect zone.

2. The method according to claim 1, wherein:
if $A_1$ is less than a given threshold value $T_1$, then the suspect zone is described as dust and eliminated, and
if $A_1$ is more than $T_1$ and if $A_2$ is more than another threshold value $T_3$ and less than another threshold value $T_2$, then the suspect zone is described as dust and eliminated.

3. The method according to claim 1, wherein the calculated phase and amplitude images of the optical component to be tested are obtained by image merging of vertical curvature $I_v$ and horizontal curvature $I_h$ data.

4. The method according to claim 1, wherein the optical component is a progressive addition lens comprising standard engravings and where the engravings are used to determine the attitude of the lens to be tested.

5. The method according to claim 1, wherein the engravings are micro-circles situated on the nasal and the temporal side of the lens.

6. The method according to claim 4, wherein the attitude of the lens to be tested is compared to the attitude of the defect free model lens and where a metrics is applied to align both attitudes if they do not coincide.

7. The method according to claim 5, wherein the attitude of the lens to be tested is compared to the attitude of the defect free model lens and where a metrics is applied to align both attitudes if they do not coincide.

8. The method according to claim 1, wherein the model image of a reflected or transmitted image of the pattern on a defect free optical component is calculated theoretically by using the design of a model optical component.

9. The method according to claim 1, wherein the model image of a reflected or transmitted image of the pattern on a defect free optical component is calculated on the basis of defect free optical component which have previously been observed and selected.

10. The method according to claim 9, wherein engraving segments of the defect free optical component are identified and replaced by an interpolated segment.

11. The method according to claim 1, wherein an adaptive filtering is applied to the images in order to spare small defect zones and homogenise larger scale defect zones, when comparing phase and amplitude images of both optical component to be tested and defect free model optical component.

12. The method according to claim 1, wherein a sensor dust filtering metrics is applied.

13. The method according to claim 1, wherein after separation of dust and noise, defects are classified in two types which are extended defects such as for example waves, polarized marks, varnish drops, conantric streaks and point defects such as for example craters, fibres, dirty inserts, handling scratches, black points, water marks.

14. The method according to claim 1, further comprising a decision step to state if the tested optical component is accepted or rejected.

15. A device for implementing the method according to claim 1, comprising means to generate a structured pattern, a screen, an optical component holder, a digital camera, image-processing means which comprise algorithms for phase extraction calculation, for conversion calculation, for derivation and/or integration calculation and means for separating dust and noise from other defects.

16. The device according to claim 15, wherein the image-processing means further include algorithms for B-spline interpolation calculation.

17. A computer program product for a data processing device, the computer program product comprising a set of instructions which, when loaded into the data-processing device, causes the device to perform the steps of the method as claimed in claim 1.

18. A computer readable medium carrying one or more sequences of instructions of the computer program product of claim 17.

19. The method as claimed in claim 1, applied to a selection method to a set of optical components.

20. The method according to claim 19, wherein the selection method is semi automatic and comprises firstly a visual test of a plurality of optical components done by an operator, where the operator selects a set of optical components which may be doubtful and where the method is applied to the set of the doubtful optical components.

* * * * *